US011490791B2

(12) United States Patent
Kielack et al.

(10) Patent No.: US 11,490,791 B2
(45) Date of Patent: Nov. 8, 2022

(54) POSITIONING SYSTEM

(71) Applicant: KARL STORZ SE & Co. KG, Tuttlingen (DE)

(72) Inventors: Robin Kielack, Tuttlingen (DE); Steffen Nann, Tuttlingen (DE); Michael Sauer, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 421 days.

(21) Appl. No.: 16/868,015

(22) Filed: May 6, 2020

(65) Prior Publication Data
US 2020/0375436 A1 Dec. 3, 2020

(30) Foreign Application Priority Data

May 28, 2019 (DE) ...................... 10 2019 114 352.7

(51) Int. Cl.
*A61B 1/31* (2006.01)
*A61B 17/34* (2006.01)
(Continued)

(52) U.S. Cl.
CPC ...... *A61B 1/00119* (2013.01); *A61B 1/00066* (2013.01); *A61B 1/00121* (2013.01);
(Continued)

(58) Field of Classification Search
CPC ........... A61B 90/50; A61B 1/317; A61B 1/32; A61B 17/176; A61B 17/3421;
(Continued)

(56) References Cited

U.S. PATENT DOCUMENTS 5,458,602 A * 10/1995 Goble ................ A61B 17/1714
606/98
5,688,284 A * 11/1997 Chervitz ............ A61B 17/1714
606/88
(Continued)

FOREIGN PATENT DOCUMENTS

DE 102010024259 A1 3/2012

OTHER PUBLICATIONS

European Search Report for corresponding European Application No. 20176170.7, dated Sep. 8, 2020.
(Continued)

*Primary Examiner* — Kevin T Truong
*Assistant Examiner* — Tracy L Kamikawa
(74) *Attorney, Agent, or Firm* — Jason H. Vick; Sheridan Ross, PC

(57) ABSTRACT

A positioning system comprising a first working element having a first tubular shaft, a second working element having a second tubular shaft, an arcuate element having a holding element and an arcuate rail, wherein the arcuate rail is disposed on the holding element and the holding element is adapted to be fixed on the receiving section by means of a fastening element, and a guiding element having a holding section and a guiding section, wherein the holding section is guided on the rail and the guiding section receives the second shaft, the holding section having a locking element securing the guiding element to the rail, wherein the locking element in a locking position blocks displacement of the holding section in a transverse direction and in a release position allows displacement of the holding section in the transverse direction.

13 Claims, 8 Drawing Sheets

(51) Int. Cl.
    *A61B 17/17*     (2006.01)
    *A61B 90/50*     (2016.01)
    *A61B 1/00*     (2006.01)
    *A61B 1/06*     (2006.01)
    *A61B 1/317*     (2006.01)

(52) U.S. Cl.
    CPC ............ *A61B 1/0661* (2013.01); *A61B 1/317* (2013.01); *A61B 17/176* (2013.01); *A61B 90/50* (2016.02); *A61B 2017/3405* (2013.01); *A61B 2017/3447* (2013.01)

(58) Field of Classification Search
    CPC ............ A61B 17/0206; A61B 17/3403; A61B 2017/3405; A61B 2017/3445; A61B 2017/3447
    See application file for complete search history.

(56) References Cited

U.S. PATENT DOCUMENTS

| | | | |
|---|---|---|---|
| 6,071,288 A | 6/2000 | Carol et al. | |
| 6,918,916 B2* | 7/2005 | Gobel | A61B 17/1714 |
| | | | 606/96 |
| 8,801,717 B2* | 8/2014 | Herdrich | A61B 17/1764 |
| | | | 606/88 |
| 9,198,676 B2* | 12/2015 | Pilgeram | A61B 17/1764 |
| 11,266,422 B2* | 3/2022 | Muser | A61B 17/1764 |
| 2003/0051591 A1 | 3/2003 | Gobel et al. | |
| 2004/0220588 A1 | 11/2004 | Kermode et al. | |
| 2008/0027457 A1 | 1/2008 | Dienst et al. | |
| 2009/0163766 A1 | 6/2009 | Torrie et al. | |
| 2011/0313478 A1 | 12/2011 | Herdrich et al. | |
| 2017/0252048 A1* | 9/2017 | Sauer | A61B 17/1714 |
| 2017/0258659 A1 | 9/2017 | Katzenstein | |

OTHER PUBLICATIONS

Karl Storz SE & Co. KG "Instruction Manual: Target Guide Model 28140ZAA" V.2.1; Mar. 2018.
German Search Report for German Application No. 10 2019 114 352.7, dated Feb. 19, 2020.

* cited by examiner

POSITIONING SYSTEM

CROSS-REFERENCE TO RELATED APPLICATIONS

This application claims priority to German patent application DE 10 2019 114 352.7, filed on May 28, 2019. The entire content of this priority application is incorporated herein by reference.

BACKGROUND

The present disclosure relates to a positioning system, the system being configured in particular as a triangulation aid.

In some surgeries it is difficult to position a surgical instrument at a defined location. It is also an additional challenge to visualize the same working area of the surgical instrument with an imaging system. Such difficulties arise, for example, when working inside a joint, because the working area can then often only be reached by a few routes, especially through a joint gap. This will be illustrated below using the example of an arthroscopy on the temporomandibular joint.

The most serious and time-consuming step in performing an arthroscopy on the temporomandibular joint is the so-called triangulation, i.e. finding the working channel with the endoscope and navigating the working channel and arthroscope together through the joint gap. The aim is to perform certain surgical steps under endoscopic view in the joint space. Complex arthroscopic microsurgery requires a detailed view of the internal structures of the joint with a correspondingly high image quality of the arthroscope. For this reason, KARL STORZ HOPKINS® arthroscopes are frequently used in such cases.

Additional trocars are positioned to allow instruments to be inserted into the joint. A number of instruments, such as grasping forceps, scissors, palpation hooks, sickle blades and probes can be used via the trocars in the joint. The successful positioning of the arthroscope and trocars has so far been based exclusively on the many years of experience of the user and can therefore only be carried out by experts.

SUMMARY

It is therefore an object to provide an improved system for positioning, with which in particular an imaging system and a surgical instrument can be reliably and precisely positioned even in hard-to-reach areas. In particular, the aim is to facilitate arthroscopy on the temporomandibular joint.

According to one aspect, this object is addressed by a positioning system comprising
a first working element comprising a first tubular shaft having a first longitudinal center axis and a receiving portion,
a second working element with a second tubular shaft having a second longitudinal center axis,
an arc element with a holding element and a curved rail extending curvedly along an arc direction, wherein the curved rail is arranged on the holding element and the holding element is configured to be detachably and positively fastened on the receiving section by a fastening element, and
a guiding element having a holding section and a guiding section, wherein the holding section is adapted to be guided on the rail and the guiding section is adapted to receive the second tubular shaft and guide it in a center direction perpendicular to the arc direction when the holding section is guided on the rail,
wherein the holding section has a locking element which is configured for positively securing the guiding element to the rail, wherein the locking element blocks displacement of the holding section in a transverse direction in a locking position and allows displacement of the holding section in the transverse direction in a release position, wherein the transverse direction is perpendicular to the direction of the arc and perpendicular to the center direction.

One of the possible applications of this system is as follows. First, the first working element is positioned in such a way that the first tubular shaft is positioned at least near the desired working area. Since the first shaft typically has an imaging system, i.e. it guides an imager or directs light to an imager via an optical system, the correct positioning of the first working element can also be checked directly. In particular, this involves the positioning of a distal section of a video endoscope, either with a distal imaging system or a proximally positioned camera head.

Then the arc element is fixed to the first working element. Specifically, a fastening element of the holding element is attached to the receiving section of the first working element. In particular, the fastening is selected so that the arc element is rigidly attached to the first working element. In other words, there is little or no relative play between the arc element and the first working element.

If at this point the guiding element is not yet positioned on the rail of the arc element, the guiding element is now positioned on the rail. There are two main possibilities for this. On the one hand, the guiding element with the holding section can be placed on the rail along the direction of the curve. Depending on the embodiment, this can also be done if the locking element is already completely or partially in the locking position. On the other hand, the retaining section can be placed on the rail from the side, i.e. from the transverse direction. In this case the locking element is in the release position. If the guiding element is then placed on the rail, the locking element is brought partially or completely into the locking position to now block displacement in the transverse direction. It should be noted that the arc direction, center direction and lateral direction form a cylindrical coordinate system.

The second working element can now be inserted into the guiding section of the guiding element. In doing so, the second working element is guided by means of the guiding section perpendicular to the direction of the arc, i.e. in the center direction, to the working area, which was identified and located at the beginning by means of the first working element. A surgical element can now be inserted into the second tubular shaft of the second working element. Due to the orientation of the second working element in the direction of the working area, the surgical element also reaches the working area. Since the imaging system, which is guided in the first tubular shaft, visualizes the working area, the arrival of the surgical instrument at the working area can now also be seen by means of the imaging system. It should be noted that the second working element can also be inserted into the guiding section with the surgical instrument already inserted in it.

Now that the first working element and the second working element are positioned as desired, the arc element is no longer required. Therefore the locking element is now transferred from the locking position to the release position. In this way, the guiding element can now be removed laterally from the rail of the arc element. This results in only a slight displacement of the second working element, which keeps the trauma for the patient low. It is also possible to rotate the first working element including the arc element slightly around the first longitudinal center axis. In this way, the rail moves out of the holding section without having to displace the guiding element. In this way, the second working element remains substantially unchanged in its positioning, so that the trauma for the patient when separating the guiding element and the arc element is minimal. Although it is in principle also possible to remove the guiding element from the rail along the direction of the arc, this is considered less preferred in view of the potentially greater trauma.

When the guiding element is detached from the arc element, the holding element of the arc element can be detached from the receiving section of the first working element. Unrestricted work can now be done using the first working element and the second working element. It should be noted that repositioning can be carried out by placing the holding element back onto the receiving section and placing the guiding element back on the rail.

This allows, among other things, the first shaft and the second shaft to be brought together in a joint, especially in a temporomandibular joint, without restricting the user's desired navigation range with respect to the first working element and the second working element in the further course of the surgical intervention. It should be noted that in certain embodiments the first shaft can be referred to as the optical shaft and the second shaft as the instrument shaft. The cross-section of the rail, i.e. perpendicular to the direction of the arc, is, in an exemplary embodiment, rectangular with rounded corners or square with rounded corners.

In an exemplary embodiment, the retaining section has a groove which can receive the rail, the locking element is configured to narrow or close the open side of the groove and thus block the displacement of the retaining section in the transverse direction.

This embodiment may be made simple and robust. It can also prevent the guiding element from becoming jammed on the rail.

In another exemplary embodiment, the rail has a chamfer facing the locking element.

This embodiment may offer a simple constructive possibility to block a displacement of the guiding element in the transverse direction.

In another exemplary embodiment, the locking element is configured as a lever that can be pivoted from the locking position to the release position and from the release position to the locking position.

This embodiment may enable simple mechanical operation. In particular, the locking element can be configured in such a way that in the locking position it rests with an inclined surface against the chamfer. In the release position, the lever moves so far away from the chamfer that the rail is released.

In another exemplary embodiment, the locking element can be moved or pivoted from the locking position to the release position and from the release position to the locking position by a set screw.

This embodiment may enable the locking element to be actuated in a well-defined manner. In particular, a first and a second locking position can be implemented. In the first locking position, the locking element blocks a displacement of the holding section in the transverse direction, but allows a displacement of the guiding element along the rail, i.e. along the direction of the curve. If the set screw is further actuated, the locking element finally presses against the rail, so that a second locking position is achieved, in which additionally a displacement of the guiding element along the rail, i.e. in the direction of the curve, is prevented. In other words, it is possible to fix the guiding element relative to the rail.

In another exemplary embodiment, the receiving section has a first groove which is at least substantially parallel to the first longitudinal center axis.

In this embodiment, the groove may offer a mechanically reliable way of fastening the fastening element of the holding element to the receiving section. In this embodiment, the base body of the receiving section can be a cuboid with a square cross-section relative to the first longitudinal center axis.

In another exemplary embodiment, the receiving section has a second groove which extends at least substantially parallel to the first longitudinal center axis and, in particular, is opposite the first groove with respect to the first longitudinal center axis.

On the one hand, this embodiment may offer the possibility of attaching the holding element in various positions on the receiving section. On the other hand, the first and second groove can be used for a stable positioning of the holding element on the receiving section.

In another exemplary embodiment, the receiving section has further grooves which run at least substantially parallel to the first longitudinal center axis and allow several receiving facilities with respect to an angle around the first longitudinal center axis.

This embodiment may make it possible to also fix the holding element in various positions on the receiving section. In some exemplary embodiments the grooves are spaced at 90° to each other in relation to the first longitudinal center axis.

In another exemplary embodiment, the fastener comprises a rocker lever having a first protrusion at a first end and an actuation surface at an opposite second end, the protrusion being adapted to engage a groove of the receiving section.

This embodiment may offer a good possibility to fix the holding element to the receiving section. The projection represents in particular the negative form of the groove, so that an at least substantially play-free fastening is possible. The rocker lever makes it easy to loosen or engage the fastening on the receiving section with one hand.

In another exemplary embodiment, the rail is bent in such a way that the center direction and an extension of the first longitudinal center axis intersect when the arc element is attached to the receiving section by the fastening element.

This embodiment may help the user to position the second working element so that the surgical instrument guided in the second shaft can be visualized by means of an imaging system on or in the first shaft.

In another exemplary embodiment, a first end of the first tubular shaft and a second end of the second tubular shaft are less than 15 mm, or less than 10 mm, or less than 5 mm apart when the arc element is fixed to the receiving section by the fastening element and the second working element is fully inserted into the guiding section.

This embodiment may allow both an imaging system guided in the first shaft and a surgical instrument guided in the second shaft to reliably reach the same working area.

In some exemplary embodiments an extension of the second longitudinal center line intersects an extension of the first longitudinal center line when the arc element is attached to the receiving section by means of the fastening element. In other exemplary embodiments the first tubular shaft is adapted to receive an imaging system or has an imaging system and the second tubular shaft is adapted to receive a surgical instrument.

It goes without saying that the features mentioned above and those to be explained below can be used not only in the combination indicated in each case, but also in other combinations or in isolation, without leaving the spirit and scope of the present disclosure.

BRIEF DESCRIPTION OF THE DRAWINGS

An exemplary embodiment according to the present disclosure is shown in the drawings and is explained in more detail in the following description. The figures show.

DETAILED DESCRIPTION

Figure 1:
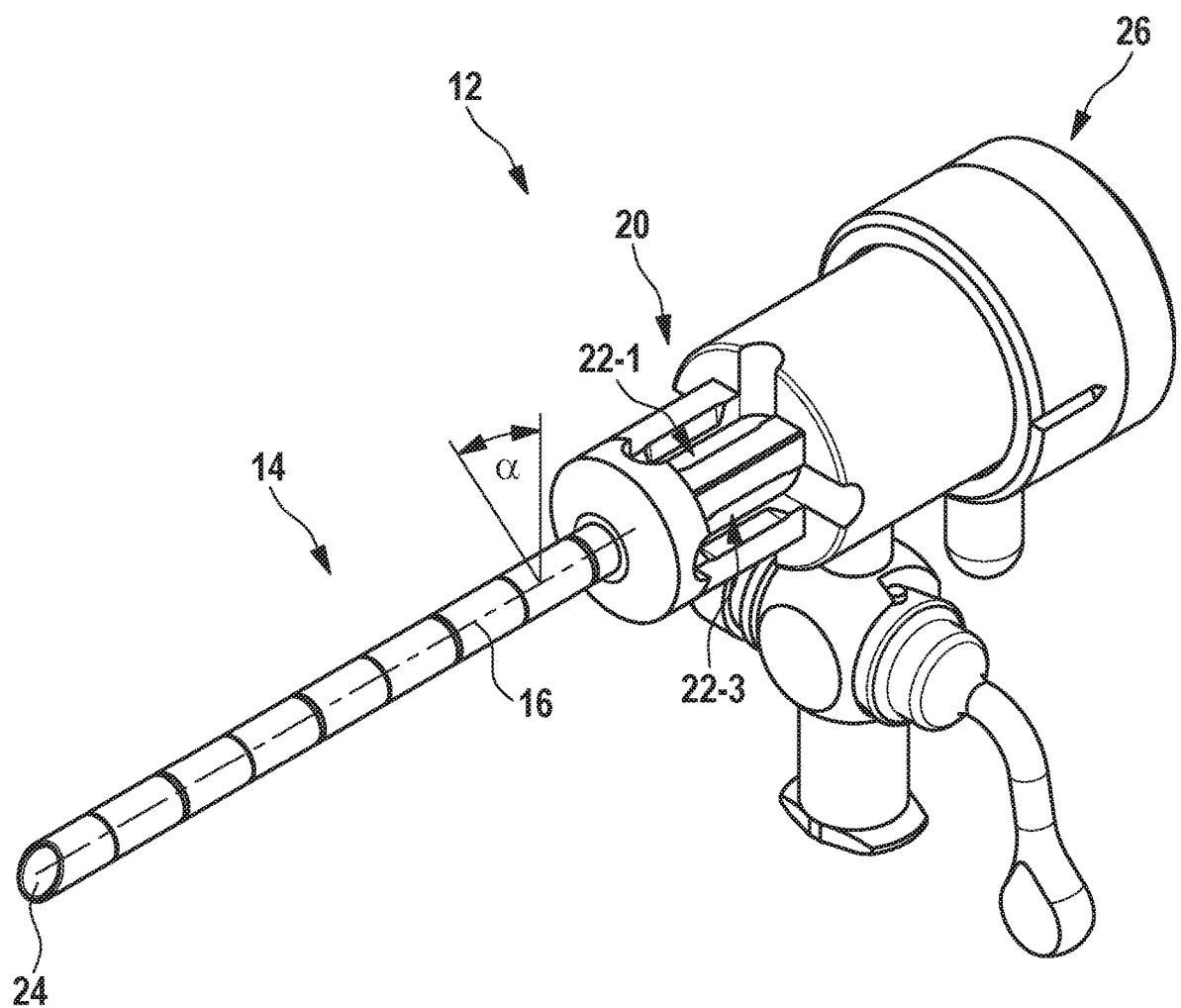
FIG. 1 a perspective view of a first working element according to an exemplary embodiment.

FIG. 1 shows a first working element 12 according to an exemplary embodiment. The first working element 12 has a first tubular shaft 14 which has a first longitudinal center axis 16. Furthermore, the first working element 12 has a receiving section 20. The receiving section 20 has a first groove 22-1, which runs parallel to the first longitudinal center axis 16. The receiving section 20 also has a second groove 22-2 (see FIG. 7), which also runs parallel to the first longitudinal center axis 16 and here, in relation to the first longitudinal center axis 16, lies opposite the first groove 22-1. The receiving section 20 also has further grooves, of which only the further groove 22-3 is visible in this perspective view and groove 22-4 (see FIG. 6) is covered. Also the other grooves run parallel to the first longitudinal center line 16 and allow several receiving facilities in relation to an angle α around the first longitudinal center axis 16.

The base body of the receiving section 20 is here a cuboid whose cross-section is square when viewed perpendicular to the first longitudinal center axis 16. Grooves 22-1, 22-2, 22-3 and 22-4 are incorporated into this cuboid.

In this embodiment, the first shaft 14 is filled with an optical system 24. Light incident from the working area at the distal end of the optical system 24 is directed towards the proximal side of the first working element 12 and can be detected there by a camera head (not shown) connected to a first port 26.

Figure 2:
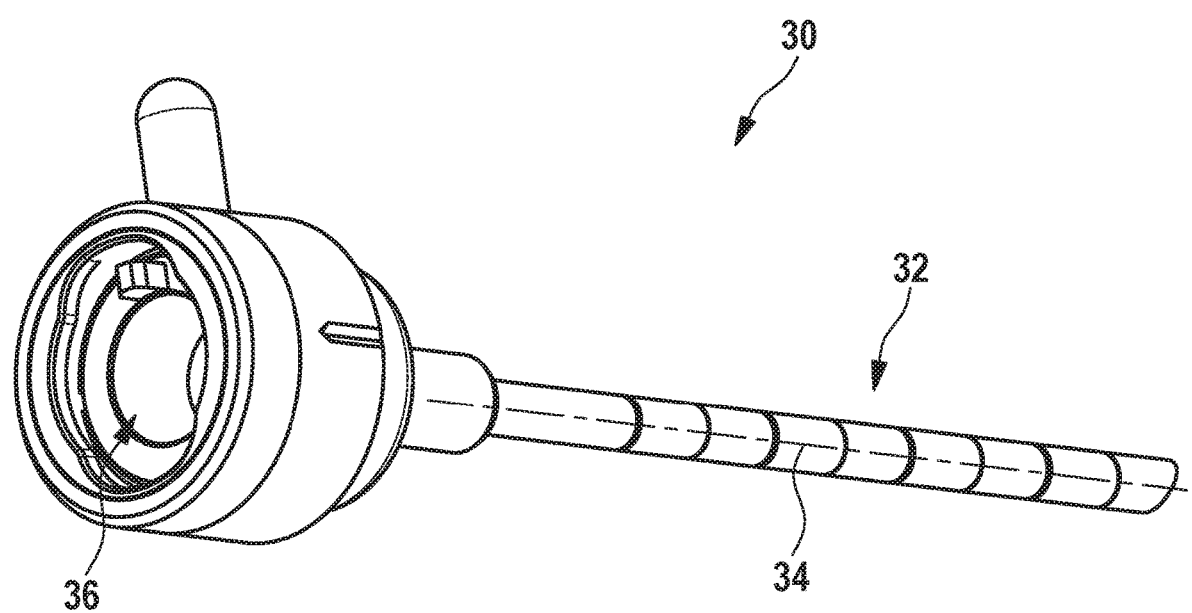
FIG. 2 a perspective view of a second working element according to the exemplary embodiment.

FIG. 2 shows a second working element 30 according to the exemplary embodiment. The second working element 30 has a second tubular shaft 32 which has a second longitudinal center axis 34. The second shaft 32 is configured to accommodate a surgical instrument (not shown). The surgical instrument can be inserted into the second shaft 32 via a second connection 36 and can also be locked at the connection point.

Figure 3:
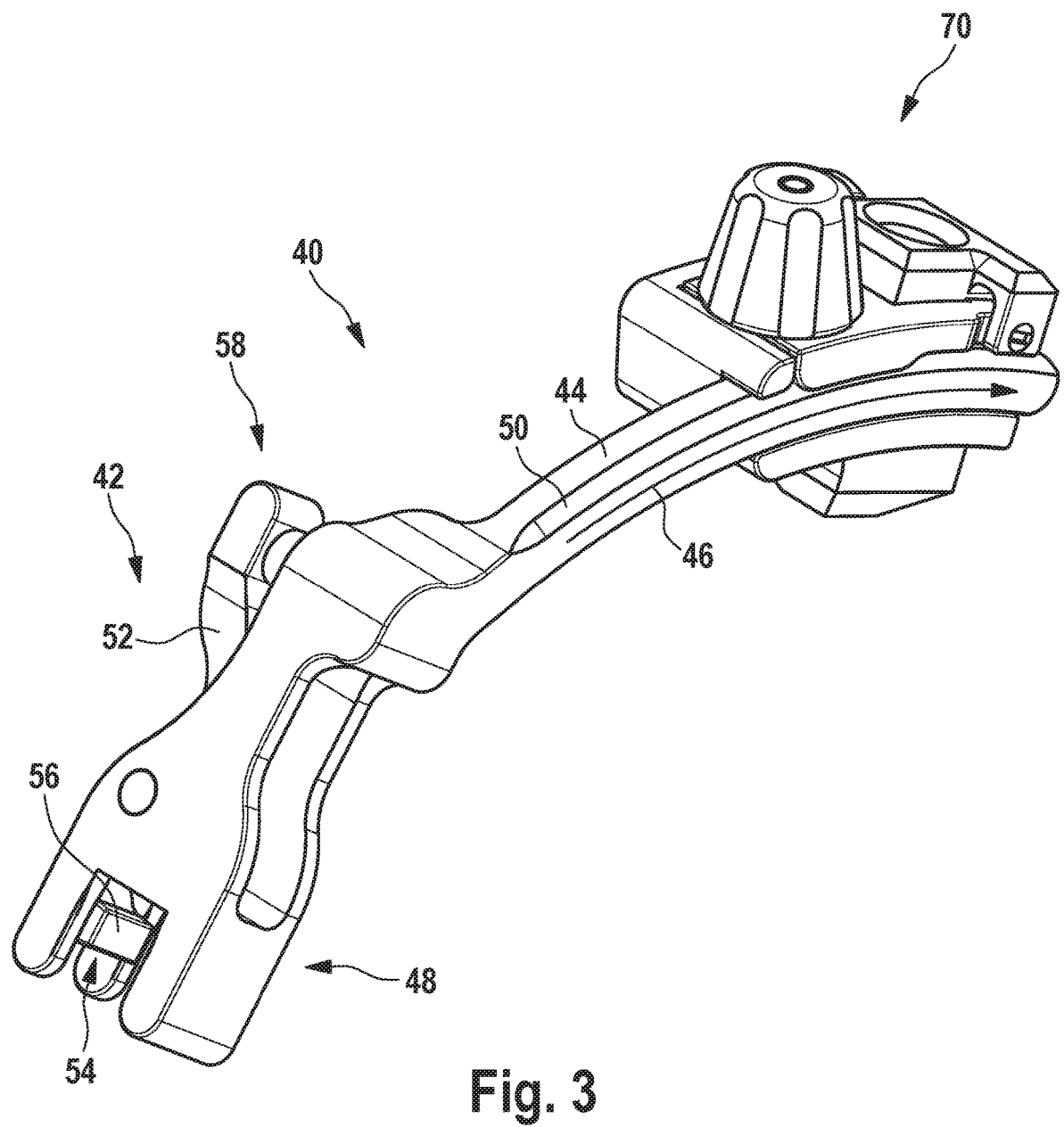
FIG. 3 a perspective view of an arc element with an attached guiding element according to the exemplary embodiment.

FIG. 3 shows an arc element 40 according to the exemplary embodiment. The guiding element 70 also shown here according to the exemplary embodiment will be explained later.

The arc element 40 has a holding element 42 and a curved rail 44, which extends along an arc direction, see arrow 46. The rail 44 is arranged on the holding element 42.

The holding element 42 is configured to be detachably and positively fastened to the receiving section 20 by means of a fastening element 48. The rail 44 has a chamfer 50.

The fastening element 48 has a rocker lever 52, which has a first projection 56 at a first end 54 and an actuation surface 60 (see FIG. 7) at an opposite second end 58. The projection 56 is configured to engage in one of the grooves 22-1, 22-2, 22-3, 22-4 of the receiving section 20. It can be seen that the fastening element 48 has a substantially rectangular or square passage. This passage can be placed onto the receiving section 20 with a positive fit, so that only a small amount of play remains during fastening. When the first projection 56 then engages in one of the grooves 22-1, 22-2, 22-3, 22-4, the arc element 40 is detachably fastened to the receiving section 20.

Figure 4:
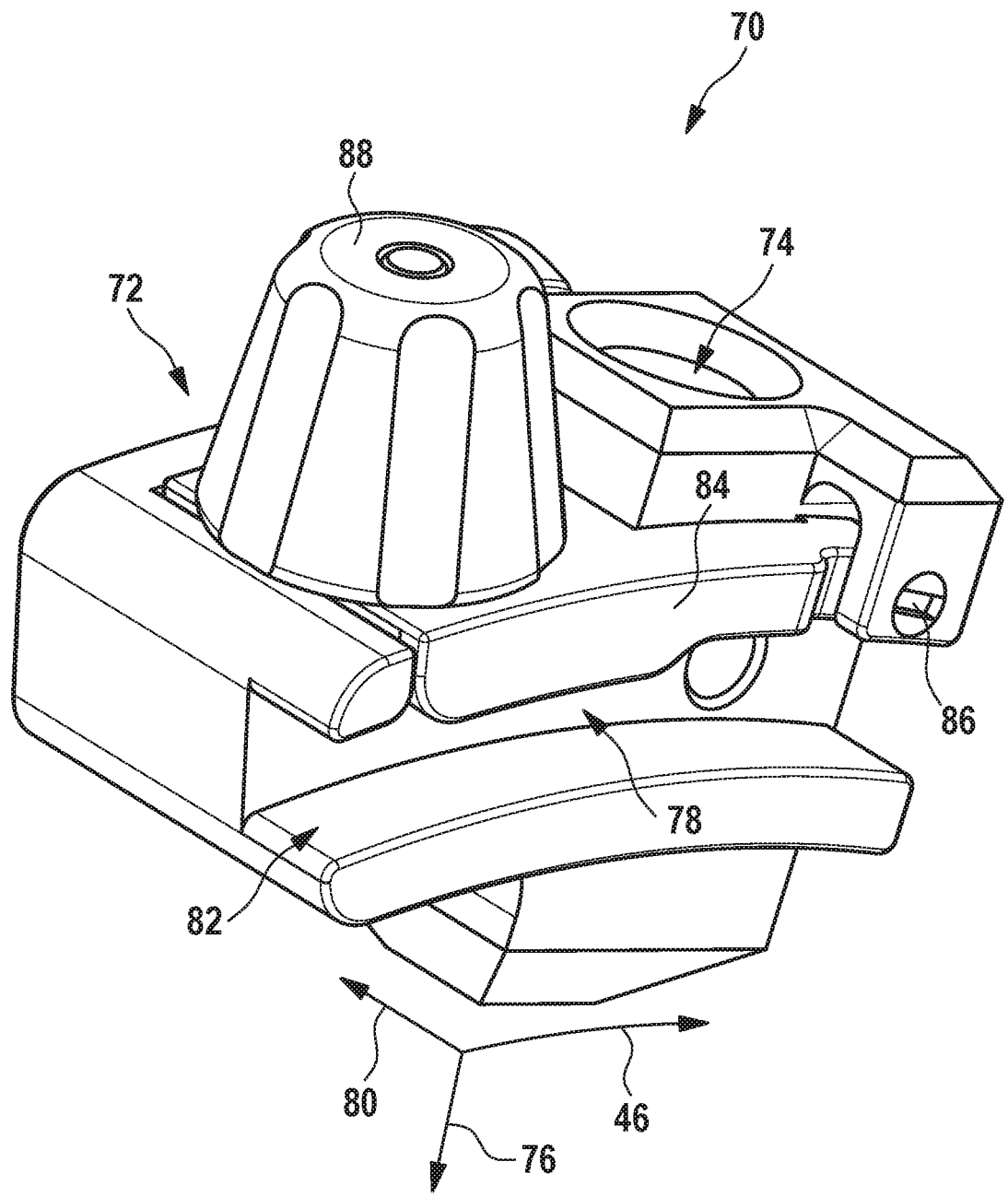
FIG. 4 a perspective view of the guiding element of FIG. 3.

FIG. 4 shows the guiding element 70 according to the exemplary embodiment. The guiding element 70 has a retaining section 72 and a guiding section 74. The retaining section 72 is configured to be guided on the rail 44. The guiding section 74 is configured to receive the second tubular shaft 32 and to guide it in a center direction, arrow 76, when the retaining section 72 is guided on the rail 44. The center direction 76 is perpendicular to the direction of the arc 46, and the holding section 72 has a locking element 78 that is configured to positively secure the guiding element 70 to the rail 44. The locking element 78 is configured to block, in a locking position, a displacement of the retaining section 72 in a transverse direction, direction symbol 80 pointing into the drawing plane. The transverse direction 80 is both perpendicular to the arc direction 46 and the center direction 76. The locking element 78 is further configured to enable a displacement of the retaining section 72 in the transverse direction 80 in a release position.

The holding section 72 has a holding groove 82 which can accommodate the rail 44. The locking element 78 is configured to narrow or slide the open side of the retaining groove 82 and thus block the displacement of retaining section 72 in the transverse direction 80.

The locking element 78 is configured as lever 84, which can be moved or pivoted from the locking position to the release position and from the release position to the locking position. The locking element 78 can be shifted or pivoted from the locking position into the release position and from the release position into the locking position by a set screw 88. Optionally, a configuration can be selected so that the locking element 78 can also be pressed against the rail 44 in order to also prevent displacement of the guiding element 70 along the rail 44.

Figure 5:
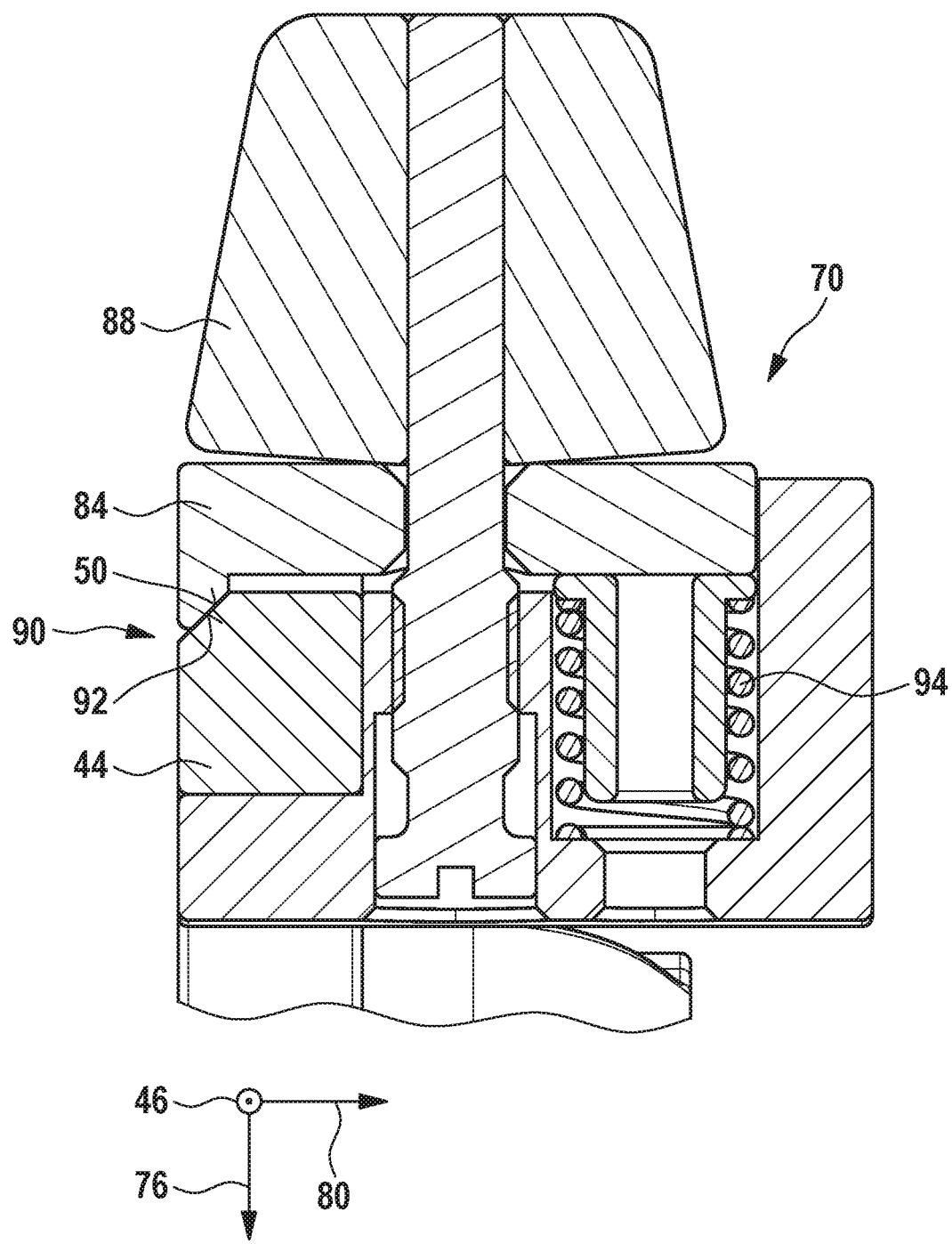
FIG. 5 a sectional view through the arc element and the guiding element of FIG. 3.

FIG. 5 shows how the interaction between the lever 84 of the locking element 78 and the rail 44 works in the exemplary embodiment. It can be seen that a section 90 of the lever 84 with an inclined surface 92 abuts the chamfer 50 of the rail 44. The guiding element 70 can now not detach from the rail 44 in the transverse direction 80. It is also optionally possible to exert sufficient pressure on the lever 84 so that the interaction of the chamfer 50 with the inclined surface 92 prevents displacement along the direction of the arc 46. If the set screw 88 is loosened, the spring 94 pushes the lever 84 outwards so that the inclined surface 92 is released from the chamfer 50. When the lever 84 has pivoted out far enough, the rail 44 is free and the guiding element 70 can be detached from the rail 44.

Figure 6:
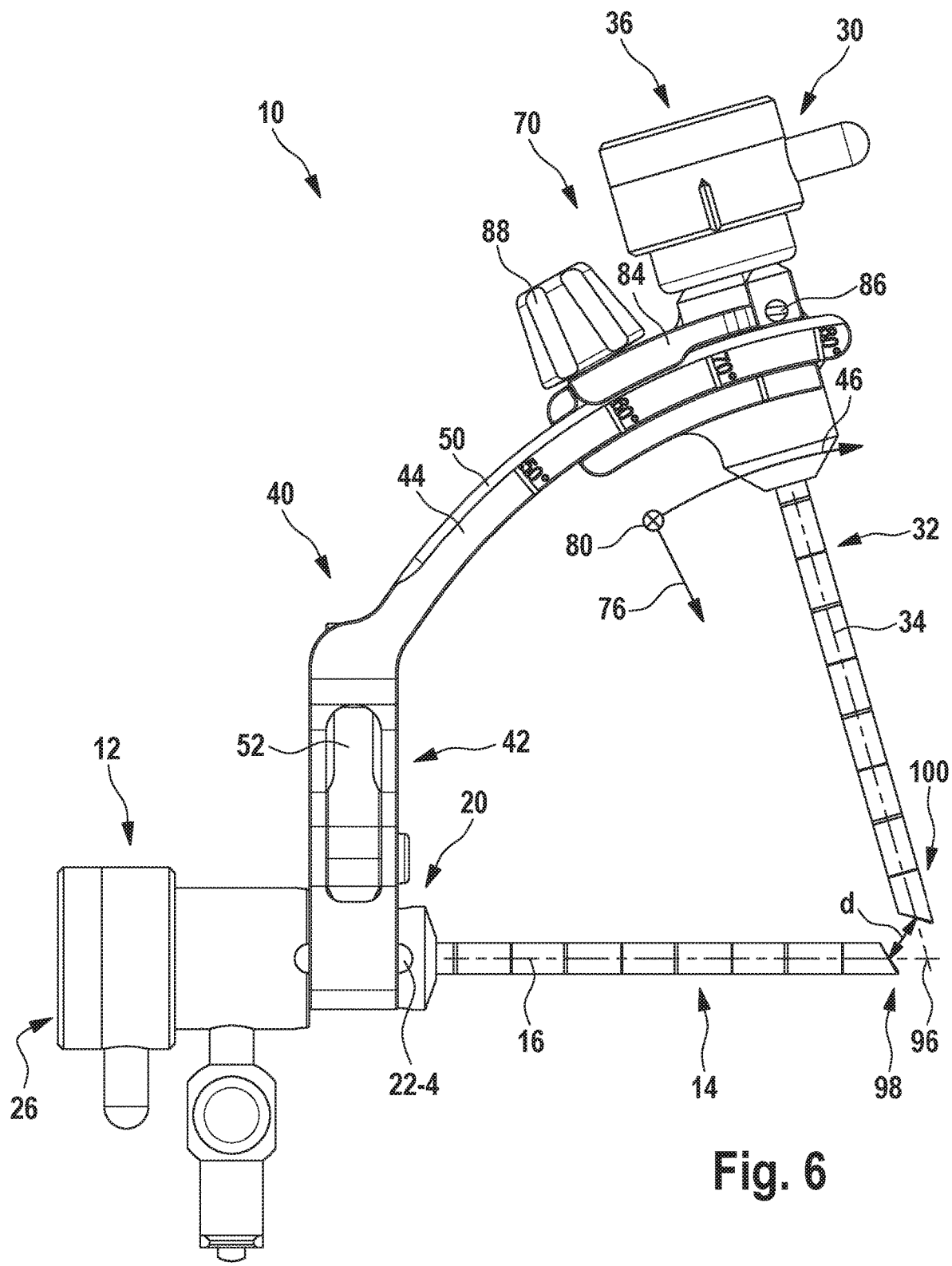
FIG. 6 a side view of a system for positioning according to the exemplary embodiment.

FIG. 6 shows a side view of a system 10 for positioning according to the exemplary embodiment. It can be seen that the arc element 40 is fixed to the receiving section 20, that the guiding element 70 is placed on the rail 44 and the second working element 30 is fully inserted into the guiding section 74.

In this FIG. 6, an intersection 96 is also shown where an extension of the first longitudinal center line 16 and an extension of the second longitudinal center line 34 intersect. In addition, a distance d is drawn between a first end 98 of the first tubular shaft 14 and a second end 100 of the second tubular shaft 32. This distance d can be chosen very small for accurate positioning, for example less than 5 mm.

Figure 7:
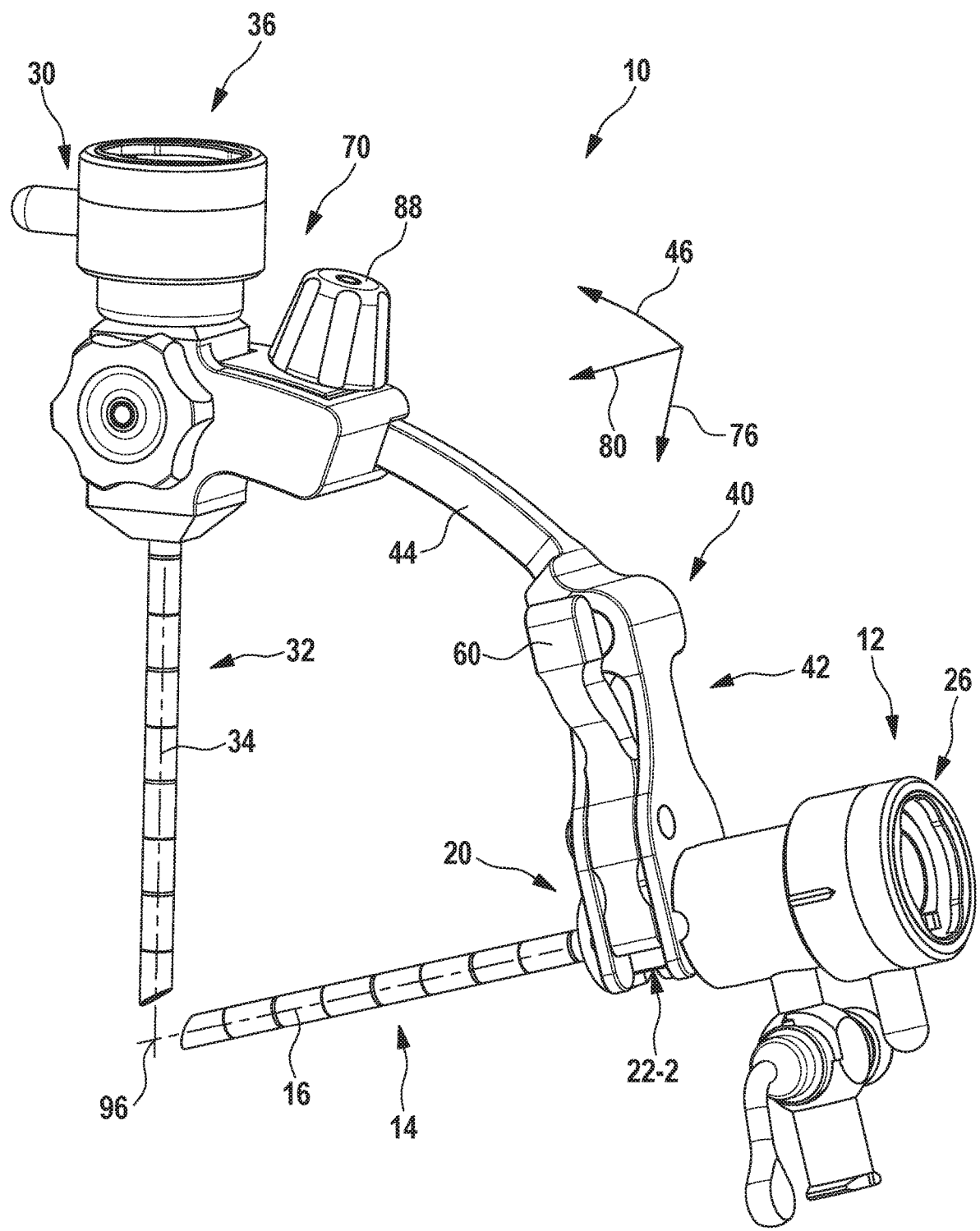
FIG. 7 a first perspective view of the system of FIG. 6.

FIG. 7 shows a first perspective view of the system 10 of FIG. 6.

Figure 8:
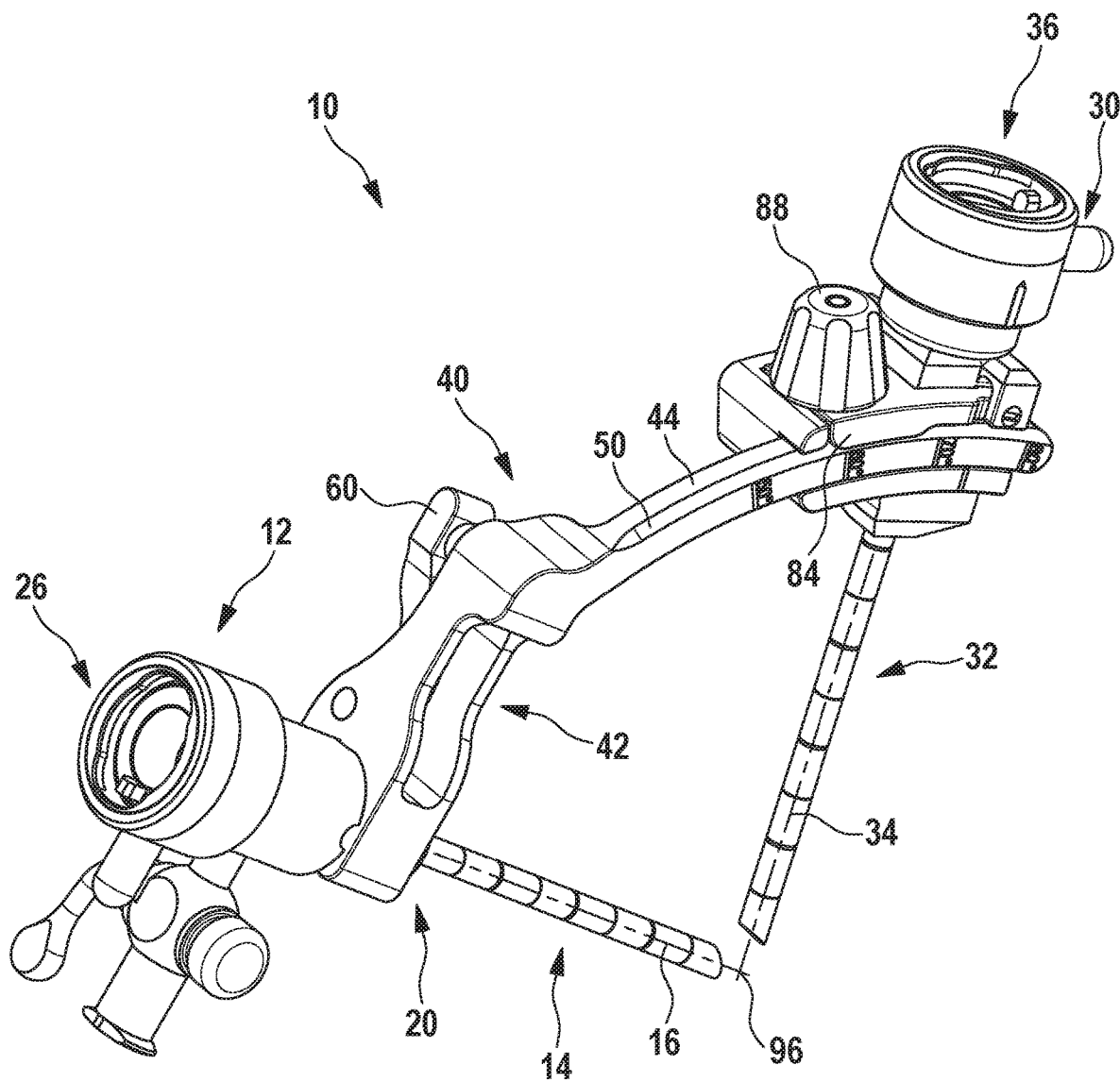
FIG. 8 a second perspective view of the system of FIG. 6.

FIG. 8 shows a second perspective view of the system 10 of FIG. 6.

The invention claimed is:

1. A positioning system comprising
a first working element having a first tubular shaft with a first longitudinal center axis and having a receiving section,
a second working element having a second tubular shaft with a second longitudinal center axis,
an arc element with a holding element and a curved rail extending curvedly along an arc direction, wherein the curved rail is arranged on the holding element and the holding element is configured to be detachably and positively fastened on the receiving section by a fastening element, and
a guiding element having a holding section and a guiding section, wherein the holding section is adapted to be guided on the rail and the guiding section is adapted to receive the second tubular shaft and guide it in a center direction perpendicular to the arc direction when the holding section is guided on the rail,
wherein the holding section has a locking element which is configured for positively securing the guiding element to the rail, wherein the locking element blocks displacement of the holding section in a transverse direction in a locking position and allows displacement of the holding section in the transverse direction in a release position, wherein the transverse direction is perpendicular to the arc direction and perpendicular to the center direction.

2. The system according to claim 1, wherein the holding section has a retaining groove which can receive the rail, wherein the locking element is configured to at least one of narrow or close an open side of the retaining groove and thus block the displacement of the holding section in the transverse direction.

3. The system according to claim 1, wherein the rail has a chamfer facing the locking element.

4. The system according to claim 3, wherein the locking element is configured as a lever which can be pivoted from the locking position into the release position and from the release position into the locking position.

5. The system according to claim 1, wherein the locking element can be at least one of displaced or pivoted from the locking position to the release position and from the release position to the locking position by a set screw.

6. The system according to claim 1, wherein the receiving section has a first groove which is at least substantially parallel to the first longitudinal center axis.

7. The system according to claim 6, wherein the receiving section has a second groove which extends at least substantially parallel to the first longitudinal center axis.

8. The system according to claim 7, wherein the second groove is opposite the first groove respect to the first longitudinal center axis.

9. The system according to claim 7, wherein the receiving section has further grooves which extend at least substantially parallel to the first longitudinal center axis and permit a plurality of orientations about the first longitudinal center axis.

10. The system according to claim 1, wherein the fastening element comprises a rocker lever having a first projection at a first end and an actuation surface at an opposite second end, wherein the projection is adapted to engage in a groove of the receiving section.

11. The system according to claim 1, wherein the rail is bent in such a way that the center direction and the first longitudinal center axis intersect when the arc element is fixed on the receiving section by the fastening element.

12. The system according to claim 1, wherein a first end of the first tubular shaft and a second end of the second tubular shaft are less than 15 mm apart when the arc element is fixed on the receiving section by the fastening element and the second working element is fully inserted into the guiding section.

13. The system according to claim 1, wherein a first end of the first tubular shaft and a second end of the second tubular shaft are less than 5 mm apart when the arc element is fixed on the receiving section by the fastening element and the second working element is fully inserted into the guiding section.

* * * * *